United States Patent [19]
Buchacher et al.

[11] Patent Number: 6,057,164
[45] Date of Patent: May 2, 2000

[54] PROCESS FOR TESTING SUITABILITY OF PROTEIN FRACTIONS CONTAINING FACTOR VIII

[75] Inventors: Andrea Buchacher, Vienna; Monika Stadler, Wienerherberg; DJuro Josic, Vienna, all of Austria

[73] Assignee: Octapharma AG, Lachen, Switzerland

[21] Appl. No.: 09/142,384

[22] PCT Filed: Mar. 1, 1997

[86] PCT No.: PCT/EP97/00703

§ 371 Date: Jan. 7, 1999

§ 102(e) Date: Jan. 7, 1999

[87] PCT Pub. No.: WO97/33178

PCT Pub. Date: Sep. 12, 1997

[30] Foreign Application Priority Data

Mar. 8, 1996 [DE] Germany .......................... 196 09 050
May 10, 1996 [DE] Germany .......................... 196 18 851

[51] Int. Cl.[7] ...................... G01N 33/558; G01N 33/561; A61K 35/14; A23J 1/00
[52] U.S. Cl. .......................... 436/514; 436/514; 436/516; 430/381; 430/383; 430/384; 430/413; 430/416; 430/417; 430/420; 430/427
[58] Field of Search ..................................... 436/514, 516; 530/383, 381, 413, 416, 417, 420, 427

[56] References Cited

U.S. PATENT DOCUMENTS 5,259,951  11/1993  Arright et al. .

FOREIGN PATENT DOCUMENTS

| 0 202 853 A2 | 5/1986 | European Pat. Off. . |
| 0 359 201 A2 | 9/1989 | European Pat. Off. . |
| 0 412 466 A2 | 8/1990 | European Pat. Off. . |
| 0 412 466 A3 | 8/1990 | European Pat. Off. . |
| WO 960257A2 | 7/1995 | WIPO . |

OTHER PUBLICATIONS

Josic et al, Purification of factor VIII and von Willbrans factor from human plasma by anion –exchange chromatography. J.chromatography, vol. 662, pp. 181–190, 1994.

Arrighi et al, Factor VIII: c Concentrate virus inactivated: progress in purification by using classic chromatographic methods. Vox Sang, von. 64, pp. 13–18, 1993.

Bihoreau et al, Isolation and characterization of different activated forms of factor VIII, the human antihemophilic A factor, European Journal of Biochemistry, 185, 111–118, 1989.

*Primary Examiner*—Nita Minnifield
*Assistant Examiner*—Padma Baskar
*Attorney, Agent, or Firm*—Jacobson, Price, Holman & Stern, PLLC

[57] ABSTRACT

The method for the aptitude testing of protein fractions containing factor VIII the further processing of which comprises a pasteurizing step is performed in such a way that the starting material is examined for fragments within a range of from 20 to 50 kD. Fragments of factor VIII within this range evidently cause inhibitor formations in patients pretreated with factor VIII. Batches contaminated with such fragments can also be utilized, i.e., for the preparation of a high purity virus-free factor VIII by size exclusion chromatography on hydrophilic materials.

5 Claims, 7 Drawing Sheets

PROCESS FOR TESTING SUITABILITY OF PROTEIN FRACTIONS CONTAINING FACTOR VIII

The present invention pertains to a method for the aptitude testing of protein fractions containing factor VIII the further processing of which comprises a pasteurizing step, as well as the utilization of batches found to be unsuitable.

Factor VIII preparations are predominantly prepared from cryoprecipitate. Applicant's preparations are prepared by purification of the redissolved cryoprecipitate with aluminum hydroxide, virus inactivation with solvents/detergents and subsequent anion exchange chromatography. Due to sharpened safety directions for virus inactivation, a pasteurizing step has been additionally performed in which the preparations are heated at 63° C.±1° C. in the presence of a stabilizer for 10 hours following the first virus inactivation.

Whereas the preparations virus-inactivated according to the solvent/detergent method alone have been applied without difficulties for years, the preparations additionally subjected to the pasteurizing step exhibited unexpected and unforeseeable inhibitor formations in patients pretreated with factor VIII. Such inhibitor formations occurred after about six weeks or later. Intensive studies had the result that such inhibitor formations had occurred in an accumulated fashion in patients treated with a particular batch or with batches of a particular origin of the cryoprecipitate.

Further intensive studies had the result that those were the only batches which contained small quantities, but altogether detectable and identifiable quantities, of factor VIII fragments within a range of from 20 to 50 kD. These fragments could not be found in any other batch or in products from competitors.

When these relationships were found, it was further revealed that the early occurrence of inhibitor formation after about six weeks had only been observed in those patients which were exclusively treated with the preparations from particular batches whereas patients in which such inhibitor formation occurred later had been treated with preparations from different batches. Thus, the conclusion could be drawn with very high certainty that those contaminants in the factor VIII containing protein fractions employed, namely cryoprecipitate of a particular origin, cause the inhibitor formations. In addition, it was established that such inhibitor formation did not occur in those patients which had already been treated for years with preparations of the same origin, but in which the pasteurizing step had not yet been performed. Thus, it has to be considered now that these fragments of factor VIII are subjected to changes in the pasteurizing step which then cause the inhibitor formation.

Thus, it has been the object of the present invention to develop an aptitude test for protein fractions containing factor VIII the further processing of which comprises a pasteurizing step. This object is achieved in a surprisingly simple manner by examining the entire starting material for fragments within a range of from 20 to 50 kD. If such fragments are not present, the starting material can be employed for the preparation of a twofold virus-inactivated product. If, in contrast, such fragments are present, then additional measures are necessary for processing such starting material into useful preparations free of side effects.

BRIEF DESCRIPTION OF THE DRAWINGS

Each of FIGS. 1 and 2 is a chromatogram of a separation performed by SDS polyacrylamide gel electrophoresis.

One possibility of further processing is the use of such starting material, for example, in the method according to the German Patent Application 196 09 050.4. In this case, a chromatographic step performed on an anion-exchanger material is followed by size exclusion chromatography on hydrophilic materials. Thus, another subject matter of the invention is the utilization of batches found to be unsuitable for the usual process.

The method for the aptitude testing of protein fractions containing factor VIII the further processing of which comprises a pasteurizing step can be performed, for example, by electrophoresis or gel permeation chromatography. If this material contains virtually no fragments within a range of from 20 to 50 kD, further examinations can be omitted. In contrast, if the material contains fragments within that range, an additional examination can be carried out to see if these are fragments of factor VIII. This can be performed, for instance, by means of appropriate antibodies. Such antibodies are commercially available, for example, from Seralab under the designation of F VIII-HC (heavy chain) from the clone 530 p.

Within the scope of Applicant's studies, it has been established that such fragments of factor VIII are generated when the starting material for factor VIII had the opportunity of reacting with thrombin or other proteases. Other proteases generating such fragments include, for instance, activated factor IX or activated factor X. Factor VIII has a molecular weight of about 300 kD. The commercial well-compatible preparations additionally contain other proteins, such as the von Willebrand factor. However, they contain only traces of products in the range of below 100 kD. In contrast, in the starting materials and final products of the batches which had resulted in the inhibitor formations, such fragments of factor VIII within a range of between 20 and 50 kD, and in part even less, could be found. However, such fragments are found to an increased extent in starting materials which had been exposed deliberately to thrombin or other proteases. Thus, the critical fragments, especially of factor VIII, can be found in protein fractions containing factor VIII which had been exposed to unallowable conditions in the preparation and storage of the cryoprecipitate.

Thus, it has now become possible according to the invention to subject all protein fractions containing factor VIII to a simple aptitude test. If the starting material contains no or but small quantities of fragments within a range of from 20 to 50 kD, such material can be used unhesitatingly for the production of factor VIII preparations which are to be subjected to a pasteurizing step. The methods of electrophoresis or gel permeation chromatography which have been usual to date are capable of detecting quantities of such fragments which are above 1%, based on the content of factor VIII. By means of appropriate antibodies, it is further possible to identify fragments of factor VIII which are present in quantities of about 0.1%, based on factor VIII.

The cryoprecipitate batches which had led to the above mentioned inhibitor formation contained clearly higher amounts of such fragments. Thus, the presence of such fragments is detectable even by electrophoresis and gel permeation chromatography.

The use and further processing of material containing the fragments according to the German Patent Application 196 09 050.4 is done, for example, by the process for the preparation of a high purity virus-free antihemophilic factor (AHF or factor VIII) by means of a multi-step chromatographic method wherein, proceeding from prepurified, AHF-containing fractions or plasma, purification in one step on at least one anion exchanger material is performed following virus inactivation, wherein a chromatographic step performed on the anionexchanger material is followed by size exclusion chromatography on hydrophilic materials.

Proceeding from AHF-containing fractions which may be enriched, for example, proceeding from cryoprecipitate or even plasma, virus inactivation is performed. Purification on ion-exchange materials is also intended. This is then followed by a further chromatographic purification step, namely as a size exclusion chromatography on hydrophilic materials. This step has the advantage that the fractions obtained thereby are characterized by an antihemophilic factor (factor VIII) of high specific activity. Surprisingly, this step removes, without a reduction in yield, inactive material which may be generated by denaturing of the active factor in the preceeding purification according to the prior art.

Preferably, the size exclusion chromatography is performed on Superose®-6 material of Pharmacia and/or so-called tentacle materials of Merck, Fractogel® BioSec. The latter material is particularly useful for efficient separation at higher flow rates. Shortened separation times reduce the tendency of the sensitive proteins to denature, and in addition, this material has a high separation capacity. In particular, it may be advantageous to use a combination of the materials mentioned, for example, by first performing separation on Fractogel® BioSec, followed by purification of the thus obtainable fraction on Superose®-6. Preferably, a design is used in which the materials are filled in columns which are connected in succession.

In addition, this method has the advantage that a separation of factor VIII and von Willebrand factor (vWF) can be achieved by performing the purification in the presence of calcium chloride.

The method is suitable for both the preparative and the analytical field. Preferably, the material used for performing the size exclusion chromatography is regenerated. Regeneration is preferably performed with an alkaline solution.

The size exclusion chromatography is preferably performed with an eluent having an osmolality of from 300 to 1,000 mOsmol/l, in particular from 400 to 800 mOsmol/l. The osmolality is preferably adjusted with physiologically acceptable salts, such as sodium chloride, and physiologically compatible buffer systems, such as citrate buffer or histidine hydrochloride. The pH value of the solvent system for performing the size exclusion chromatography is pH 7 to 8.

The material thus obtained is already suitable for use with human patients and has the advantage over conventional materials that the material thus obtained has a high specific activity and therefore is not loaded with inactive protein fractions.

The factor obtainable by this method is novel because of its higher activity, not found in the prior art.

A commercial factor VIII preparation usually contains 1,000 International Units (IU) of factor VIII as determined according to the one-step test or chromogenically. About 300 to 600 International Units of von Willebrand factor (vWF) as measured according to the immunological test using anti-vWF antibodies (ELISA) is contained in commercial preparations. The protein content of such preparations is from 5 to 25 mg of protein of which about 20 to 70% falls to the active component consisting of a complex of factor VIII/vWF. The remaining protein content of 30 to 80% falls, depending on the batch, to non-active components which can be removed.

Figure 1:
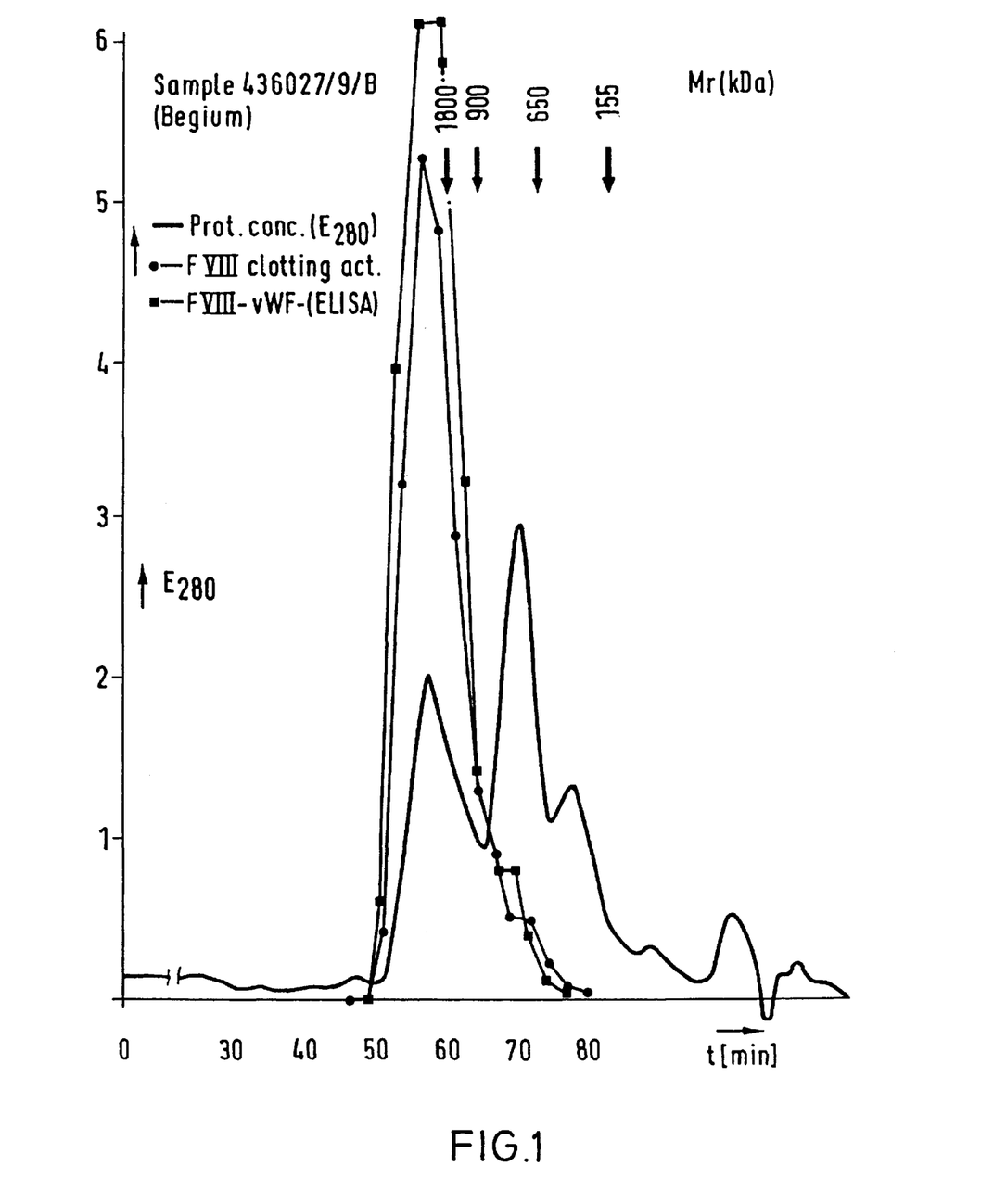

The analytical procedure is performed as follows:

The sample to be purified is dissolved in 4 ml of bidistilled water for injections and contains 250 IU of factor VIII/ml. Superose 6, analytical grade, is selected as the separation column for the size exclusion chromatography and employed in a column of 300×10 mm of inside diameter. As the mobile phase, 200 mM NaCl, buffered with 50 mM Tris-HCl, is employed at a pH value of 7.4 and an osmolality of from 450 to 500 mOsmol/l. The column is preliminarily washed with 3 column volumes of bidistilled water and optionally regenerated. If regeneration is performed, the regenerating agent is neutralized with the corresponding acid or base, and the desired pH value is adjusted by washing with 3 column volumes of 250 mM Tris.HCl at pH 8.0. Thereafter, the column is equilibrated with 3 column volumes of mobile phase. The flow rate of the mobile phase is about 0.5 ml/min. The HPLC equipment employed consists of a microprocessor controlled pump and a UV spectral photometer. The detection of any passing components is performed at a wavelength of 280 nm. The separated fractions were subsequently collected with a fraction collector, analyzed for their protein contents and for factor VIII and vWF activities, and thereafter isolated by SDS-polyacrylamide gel electrophoresis (SDS-PAGE). The applied sample quantity was 0.5 ml, corresponding to an amount of 110 to 150 International Units of factor VIII. The separation was performed at room temperature at a pressure of 5 to 15 bar. The recovery of factor VIII amounted to 85 to 95%, that of the von Willebrand factor was 70 to 90%. The corresponding chromatogram is shown in FIG. 1.

Figure 2:
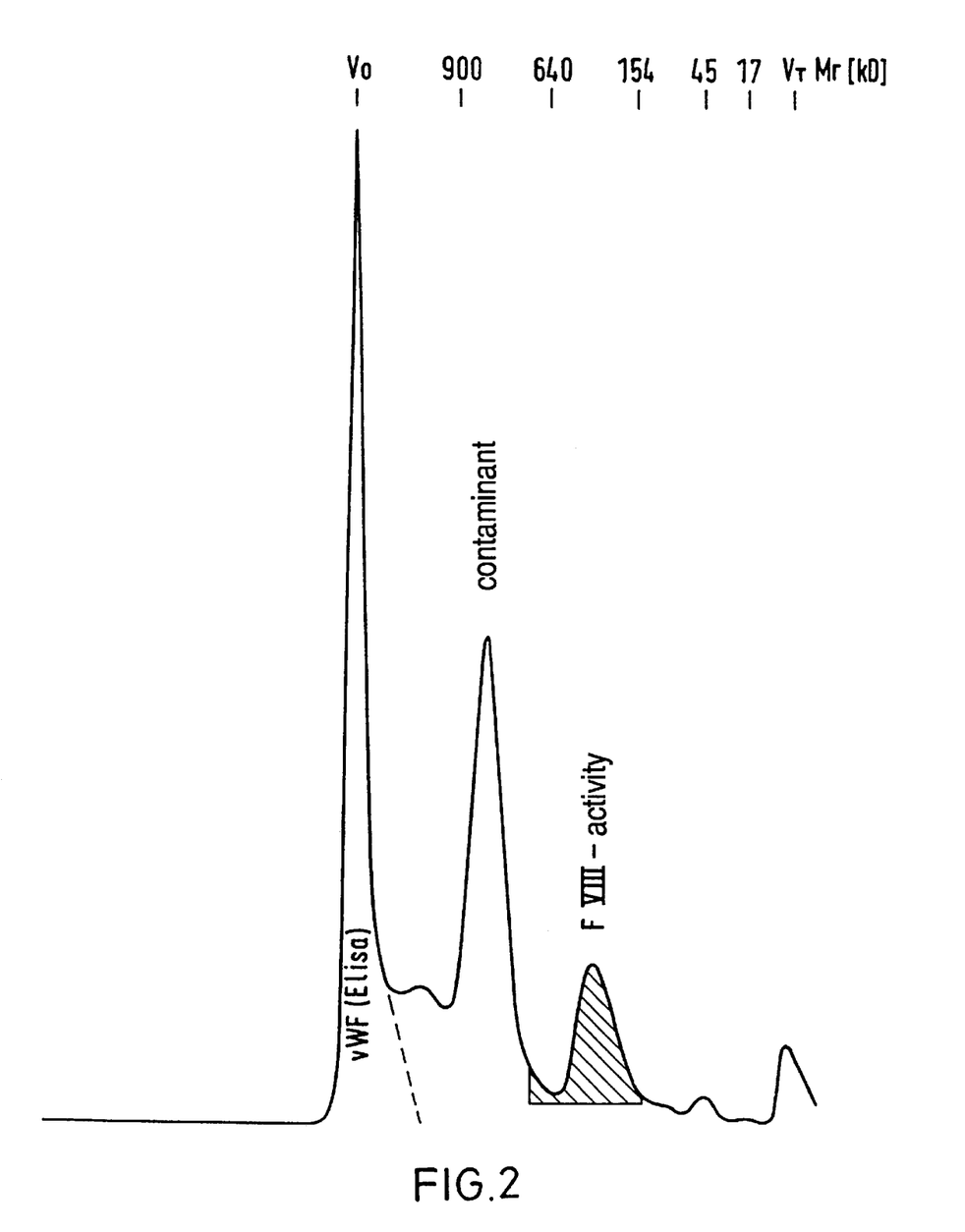

Separation of factor VIII and von Willebrand factor in the presence of calcium chloride is performed as follows:

The complex of factor VIII/vWF will dissociate in the presence of high concentrations of calcium chloride. For obtaining factor VIII free of von Willebrand factor, the purified factor VIII/vWF complex can be dissociated in a 250 mM calcium chloride solution. The subsequent separation can be effected by size exclusion chromatography according to molecular size. The sample containing factor VIII/vWF complex is purified from nonactive proteins and dialyzed against 250 mM calcium chloride solution. The concentration was 250 IU of factor VIII/ml and 150 IU of vWF/ml. The applied protein quantity was 500 μl. A column filled with Superose 6 (analytical grade) and having 300×10 mm of inside diameter was employed. In this case, a solution of 250 mM calcium chloride, 25 mM Tris.HCl, at a pH value of 7.4, served as the mobile phase. The flow rate was 0.5 ml/min. The same equipment was used as mentioned above. The recovery of factor VIII was 70 to 80%, that of von Willebrand factor was 85 to 95%. The chromatogram is shown in FIG. 2.

Figure 4:
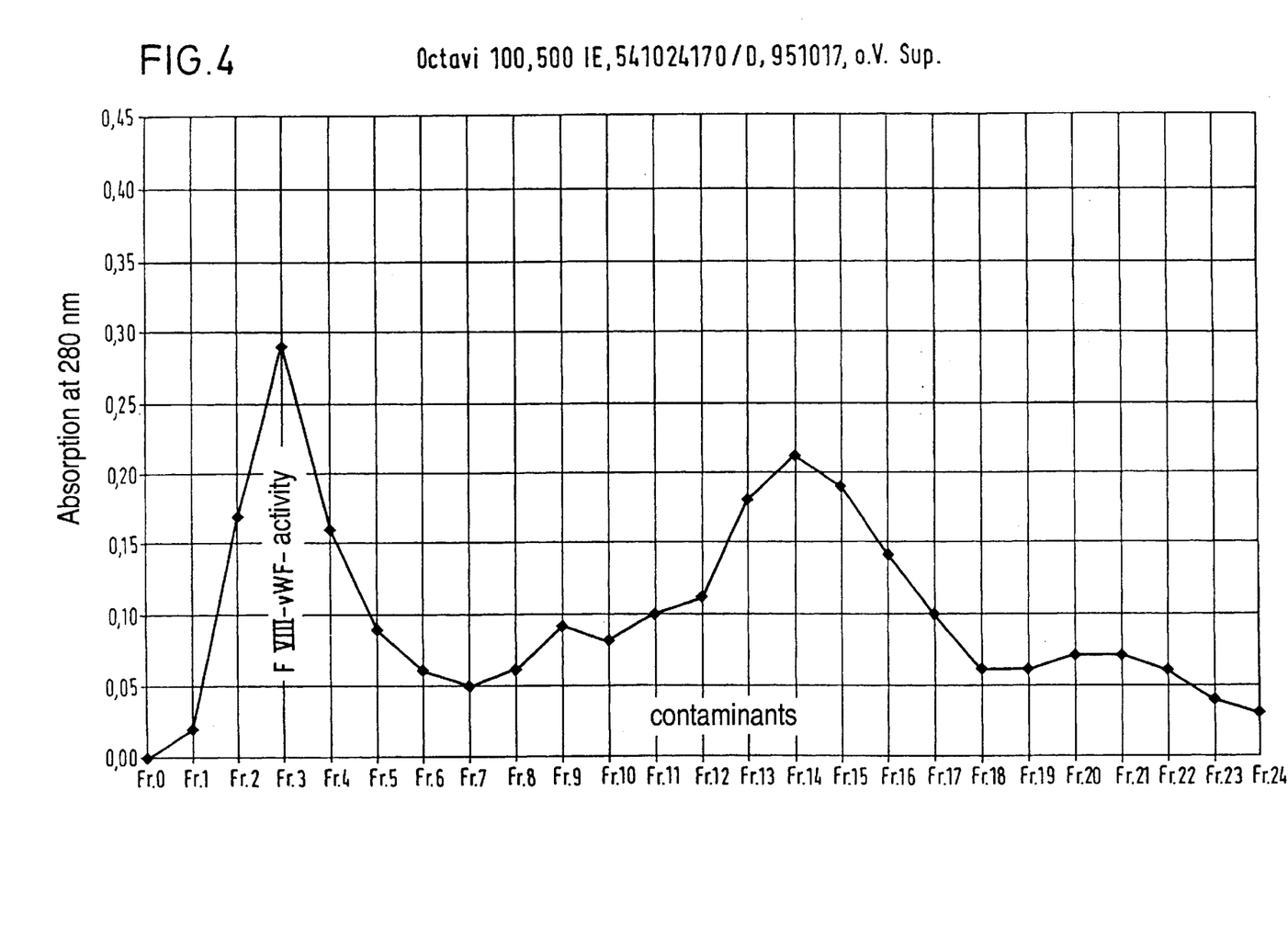
FIG. 4 is a chromatogram of size exclusion (chromatography) performed on Superose 6.
Figure 5:
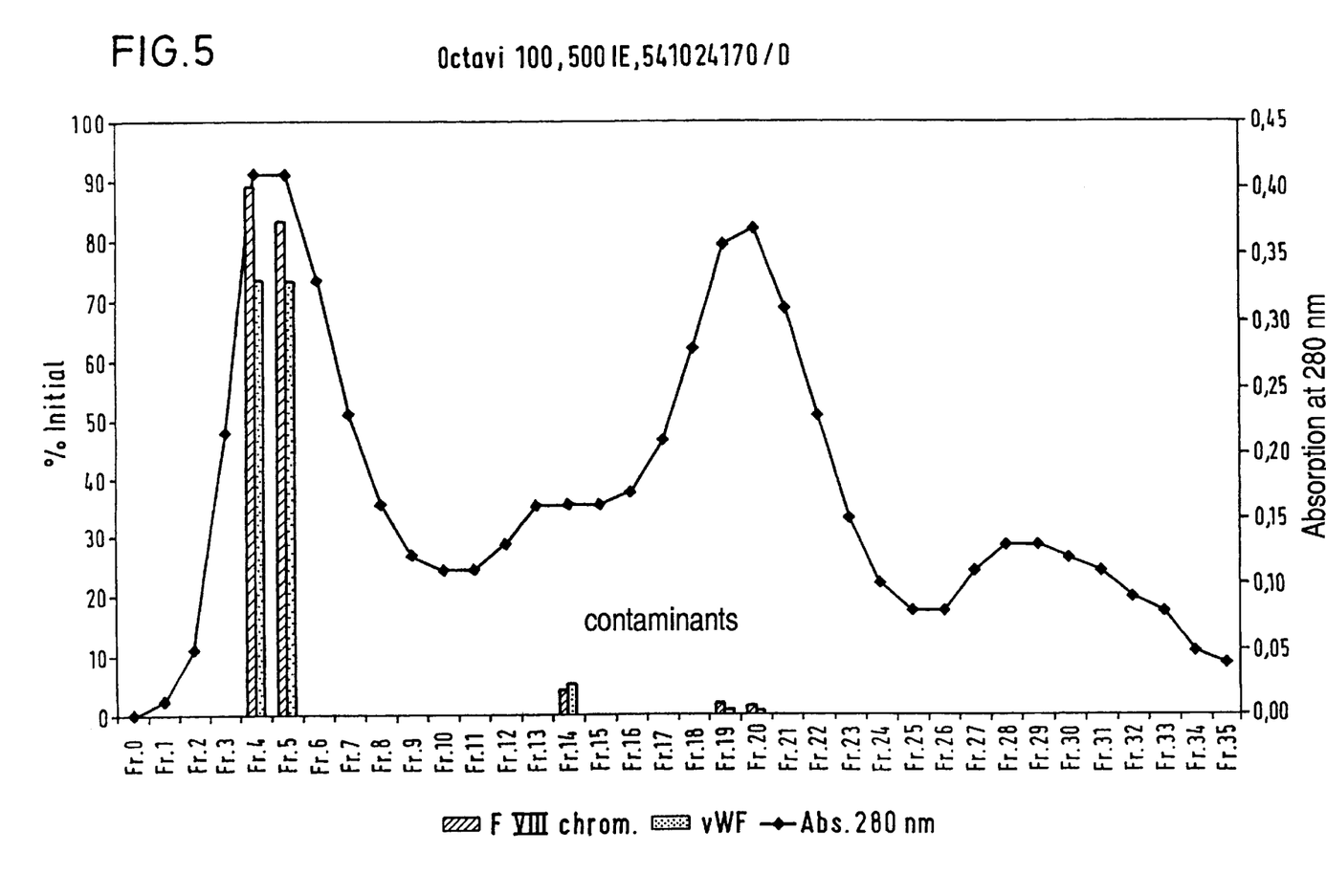
FIG. 5 is a chromatogram of size exclusion (chromatography) performed in tandem, first, on Fractogel BioSEC and, second, on Superose 6.

Semipreparative and preparative separations are performed as follows:

The separations described above can also be performed on a semipreparative or preparative scale. Fractogel BioSEC and Superose 6 (preparative column) are the materials which may be employed here. The results obtained with these materials are shown in FIGS. 3 to 5.

Figure 3:
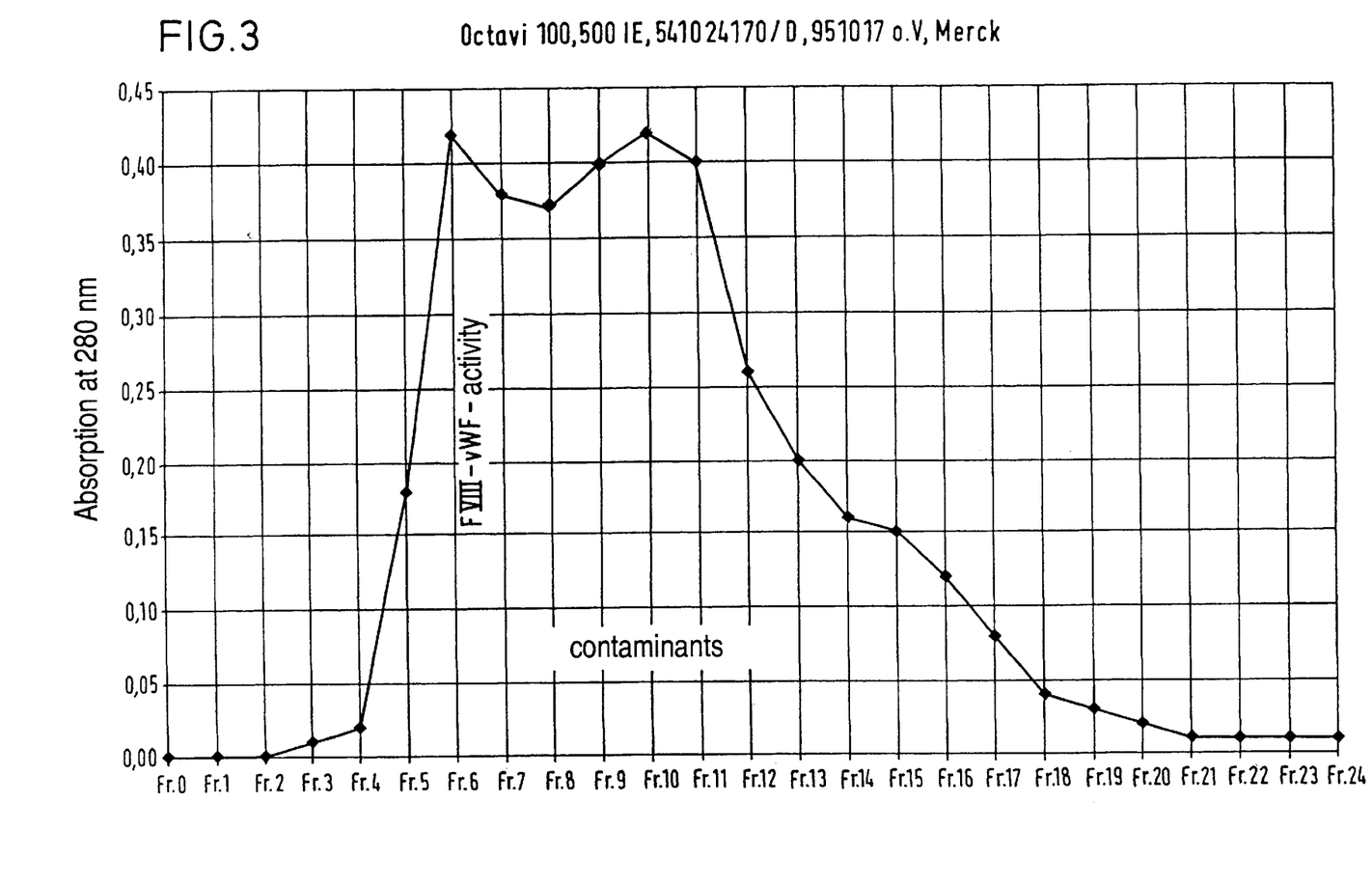
FIG. 3 is a chromatogram of size exclusion (chromatography) performed on Fractogel BioSEC.

FIG. 3 shows a size exclusion chromatography of a factor VIII/vWF complex in admixture with active proteins on a semipreparative column with Fractogel BioSEC (tentacle) support. The separation conditions are as follows:

column dimensions: 600×26 mm (bed depth: 570 mm)

mobile phase: 200 mM NaCl, 50 mM Tris.HCl, pH 7.4 osmolality: 450 to 500 mOsmol/l equipment: low-pressure pump (Pharmacia) and photometer with a fixed wavelength of 280 nm and a preparative cell. The fractions were collected and evaluated as described in Examples 1 and 2. The flow rate was 1.5 ml/min at a pressure of less than 2 bar at room temperature. The sample volume was 8 ml with 2000 International Units of factor VIII and 1280 International Units of von Willebrand factor. The recovery was 90 to 95% of factor VIII and 80 to 90% of von Willebrand factor.

Size exclusion chromatography on Superose 6 (prep. grade) support can be performed as follows:

A separation was performed on Superose 6 (prep. grade) material. The column dimensions were 600×26 mm (bed depth 550 mm), the flow rate was 1.5 ml/min, the pressure was 2 to 4 bar. The sample volume corresponded to that mentioned above. The recovery was 80 to 95% of factor VIII and 80 to 95% of von Willebrand factor. As can be seen from FIG. 4, the separation result is better than that of FIG. 3, the contaminants in the form of foreign proteins being farther separated.

Size exclusion chromatography of a factor VIII/vWF complex in admixture with non-active proteins:

Size exclusion chromatography of a factor VIII/vWF complex in admixture with non-active proteins was performed on a column tandem in which a semipreparative Fractogel BioSEC column and Superose 6 (prep. grade) column were connected in succession. The columns correspond to what has been described above. The flow rate was 1.5 ml/min at a pressure of less than 2 bar. The sample volume was 15 ml with 4500 International Units of factor VIII and 2600 International Units of von Willebrand factor. As can be seen from FIG. 5, the separation between factor VIII/von Willebrand complex and the foreign proteins is very good. The use of the tandem column has the advantage of highly reducing cloggings of the Superose 6 column.

Figure 6:
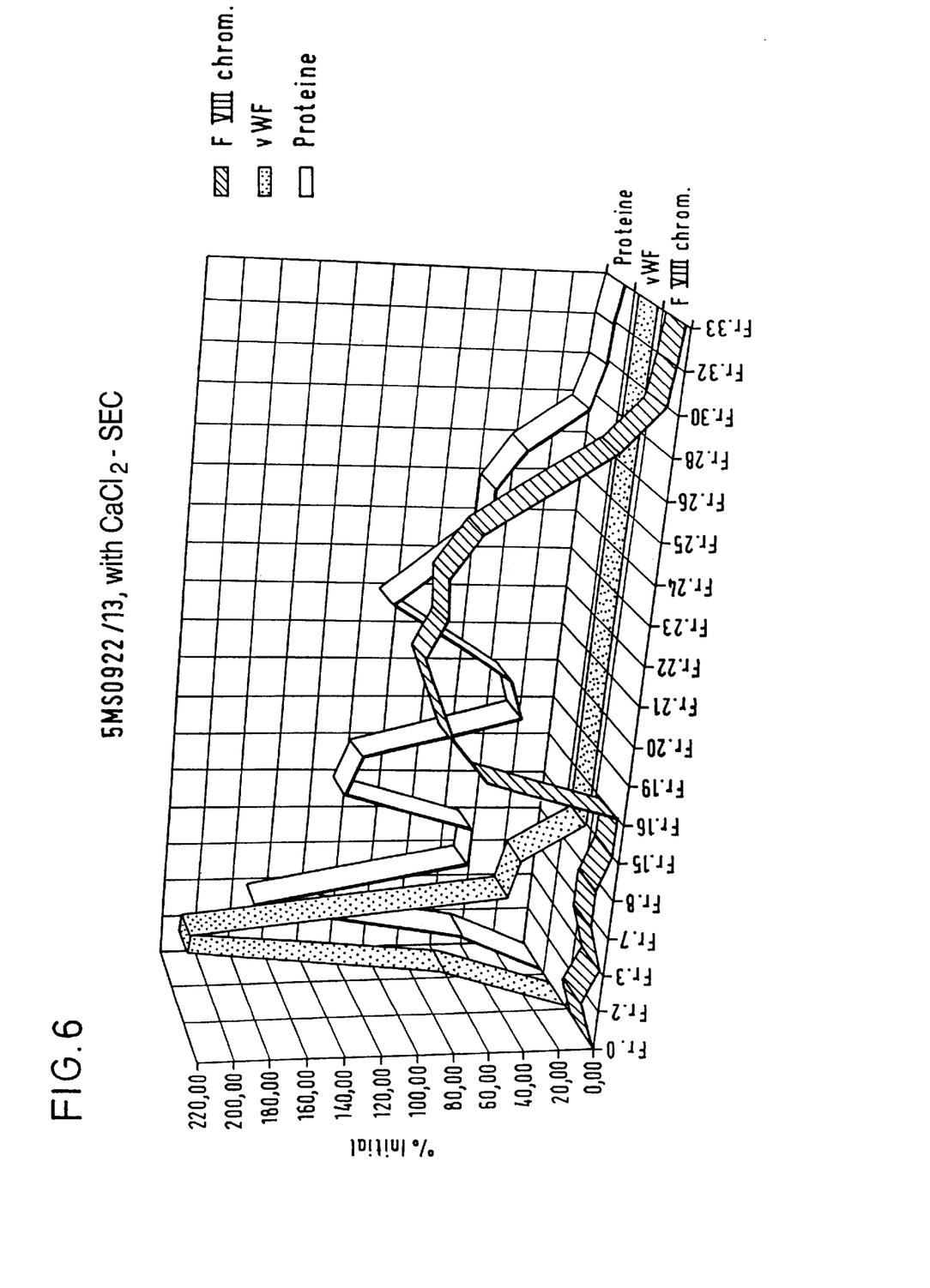
FIG. 6 represents comparative results of size exclusion chromatography performed in tandem (as described above) on Fractogel BioSEC and Superose 6.

Semipreparative separation of factor VIII/von Willebrand complex in the presence of a high concentration of calcium ions is performed as follows:

A column tandem is used consisting of a Fractogel BioSEC and a Superose 6 (prep. grade) column. Semipreparative separation of factor VIII and von Willebrand factor is performed in the presence of 250 mM calcium chloride solution. A quantity of 12 ml with 3000 International Units of factor VIII and 1800 International Units of von Willebrand factor was applied. The mobile phase was a solution of 250 mM calcium chloride and 25 mM Tris.HCl at pH 7.4. The recovery of von Willebrand factor was 90 to 95%, and that of factor VIII was 75 to 90%. The results are represented in FIG. 6.

Figure 7:
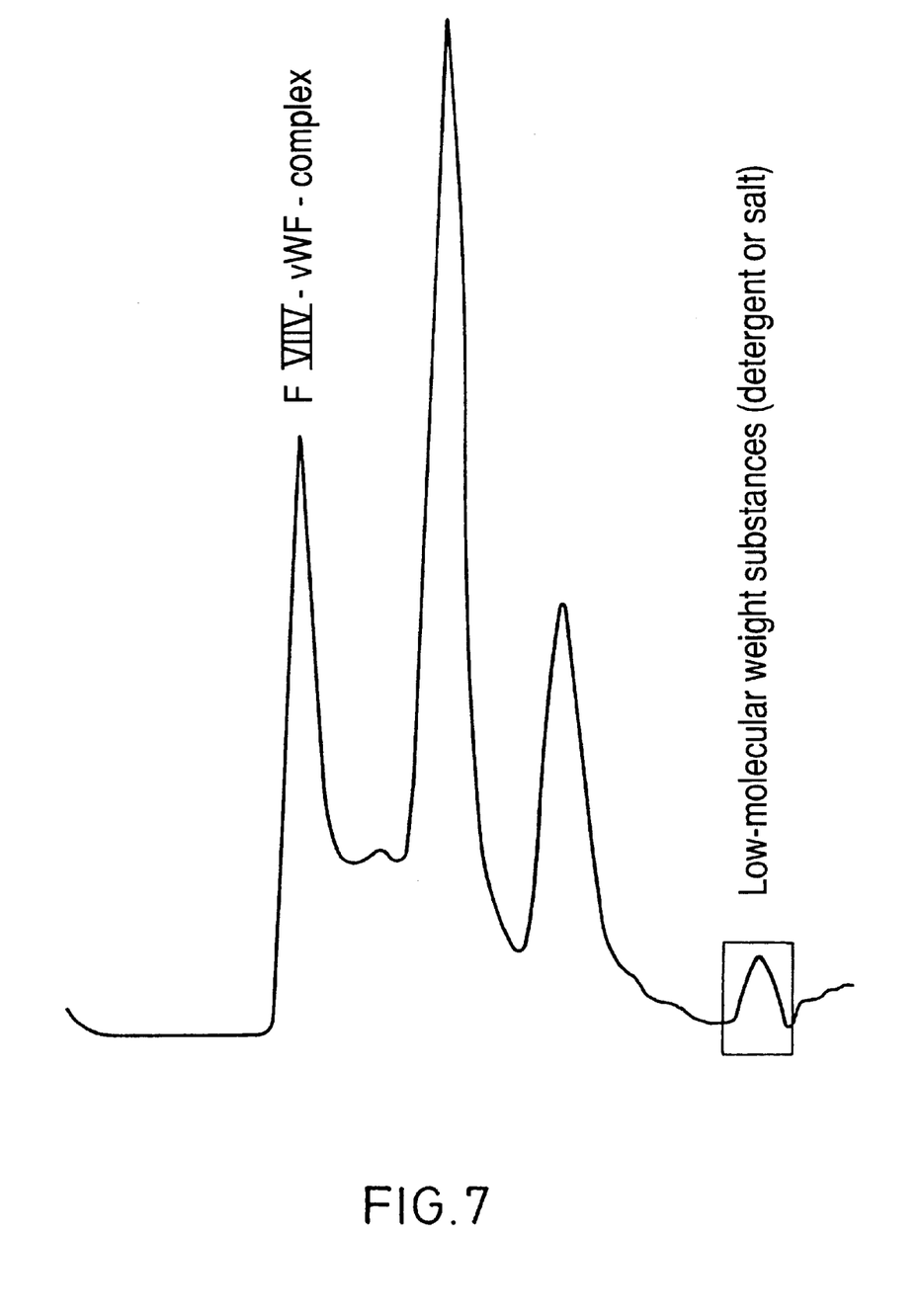
FIG. 7 is a chromatogram of size exclusion (chromatography) affected between proteins and detergents.

Separation of detergents with size exclusion chromatography and rebuffering is performed as follows:

FIG. 7 shows that detergents or ions can be separated off very advantageously by size exclusion chromatography so that the factor VIII/von Willebrand complex fraction obtained in the size exclusion chromatography can be used directly as a therapeutic agent after adjusting to physiological conditions or collection and freeze-drying.

What is claimed is:

1. A method for testing protein fractions containing factor VIII for further processing which requires a pasteurizing step, comprising screening of said protein fractions for fragments within a range 20 to 50 kD.

2. The method according to claim 1, wherein screening is directed to identifying fragments of factor VIII.

3. The method according to claim 2, wherein identifying said fragments of factor VIII is effected by means of antibodies.

4. The method according to claim 1, wherein screening is performed by electrophoresis or gel permeation chromatography.

5. A method for preparing high purity virus-free antihemophilic factor, said method comprising:

screening protein fractions containing factor VIII for fragments within a range 20 to 50 kD;

identifying the protein fraction having said fractions;

combining together said protein fractions having said fragments to form a fraction batch;

virus inactivating said batch;

applying said batch on at least one anion-exchanger material; followed by performing a chromatographic step on the anion-exchanger material to obtain hydrophilic materials; followed by performing size exclusion chromatography on said hydrophilic materials.

* * * * *